US010632144B2

United States Patent
Bazza et al.

(10) Patent No.: US 10,632,144 B2
(45) Date of Patent: Apr. 28, 2020

(54) LOW POLYDISPERSITY, LOW MOLECULAR WEIGHT BIOTECHNOLOGICAL CHONDROITIN SULFATE WITH ANTI-INFLAMMATORY AND ANTIARTHRITIS ACTIVITY AND USE THEREOF IN THE PREVENTION OF OSTEOARTHRITIS

(71) Applicant: Gnosis S.p.A., Milan (IT)

(72) Inventors: Paola Bazza, Casateneovo (IT); Davide Bianchi, Desio (IT); Niccolo Miraglia, Desio (IT); Marco Valetti, Desio (IT); Ermanno Valoti, Dalmine (IT); Nicola Angelo Maria Volpi, Modena (IT)

(73) Assignee: Gnosis S.p.A., Milan (IT)

( * ) Notice: Subject to any disclaimer, the term of this patent is extended or adjusted under 35 U.S.C. 154(b) by 0 days.

(21) Appl. No.: 16/144,758

(22) Filed: Sep. 27, 2018

(65) Prior Publication Data

US 2019/0231810 A1   Aug. 1, 2019

Related U.S. Application Data (63) Continuation-in-part of application No. 14/947,634, filed on Nov. 20, 2015, now abandoned, which is a continuation of application No. 14/402,646, filed as application No. PCT/EP2013/060471 on May 22, 2013, now abandoned.

(30) Foreign Application Priority Data

May 22, 2012   (IT) .............. MI2012A0880

(51) Int. Cl.
| | | |
|---|---|---|
| A61K 31/737 | (2006.01) |
| C08B 37/00 | (2006.01) |
| A61K 31/726 | (2006.01) |
| A61K 31/375 | (2006.01) |
| A61K 45/06 | (2006.01) |

(52) U.S. Cl.
CPC .......... *A61K 31/737* (2013.01); *A61K 31/375* (2013.01); *A61K 31/726* (2013.01); *A61K 45/06* (2013.01); *C08B 37/0069* (2013.01)

(58) Field of Classification Search
None
See application file for complete search history.

(56) References Cited

U.S. PATENT DOCUMENTS

2012/0289477 A1* 11/2012 Bianchi ............... A61K 31/737
  514/54
2012/0295865 A1* 11/2012 Valoti ................. C08B 37/0069
  514/53

FOREIGN PATENT DOCUMENTS

WO   2005110438 A2   11/2005

OTHER PUBLICATIONS

International Search Report and Written Opinion (ISA/EP) of Appln. No. PCT/EP2013/060471 dated Jul. 1, 2013.
Cho So Yean et al "Effects of low molecular weight chondroitin sulfate on type II collagen-induced arthritis in DBA/1J mice", Biological & Pharmaceutical Bulletin (of Japan), Pharmaceutical Society of Japan, vol. 27, No. 1, pp. 47-51 Jan. 1, 2004.
Volpi "Influence of charge density, sulfate group position and molecular mass on adsorption of chondroitin sulfate onto coral", Biomaterials, Elsevier Science Publishers, vol. 23 No. 14, pp. 3015-3022, Jul. 1, 2002.
Tsutsumi et al "Functional expression and genomic structure of human chondroitin 6-sulfotransferase", FEBS Letters, Elsevier, vol. 441 No. 2, pp. 235-241, Dec. 18, 1998.
Rodriguez et al "Structure and serological characteristics of the capsular K4 antigen of *Escherichia coli* 05:K4:H4, a fructose-containing polysaccahride with a chondroitin backbone", European Journal of Biochemistry, Blackwell Publishing, vol. 177 No. 1, pp. 117-124, Jan. 1, 1988.
Cho, Effects of low molecular weight chondroitin sulfate on type II collagen-induced arthritis in DBA/1J mice. Bioi. Pharm. Bull. 27(1) 47-51 (2004).
Merck Manuals, Osteoarthritis, downloaded from the internet May 15, 2015.
TPIMS, Inflammatory Disorders, internet article, http://www.tpims.org/disease-research/inflammatory-disorders, 2013.
International Preliminary Report on Patentability (PCT/IPEA/409) of Appln. No. PCT/EP2013/060471 dated Jun. 6, 2014.

\* cited by examiner

*Primary Examiner* — Layla D Berry
(74) *Attorney, Agent, or Firm* — Amin Talati Wasserman LLP; Valerie Neymeyer-Tynkov; George M. Carrera, Jr.

(57) ABSTRACT

Disclosed is a low molecular weight (1000-5000 daltons) chondroitin sulfate (CS) produced by chemical sulfation of a non-sulfated chondroitin backbone (K4 capsular polysaccharide) obtained with biotechnology techniques. The CS described is substantially monosulfated, mainly at the 6-position, with very little sulfation at the 4-position, and with a mono/disulfated disaccharide ratio and charge density similar to those of natural CS. Said biotechnological chondroitin sulfate (CS) is useful in the treatment and prevention of osteoarthritis and in acute and chronic inflammatory processes.

17 Claims, 7 Drawing Sheets

LOW POLYDISPERSITY, LOW MOLECULAR WEIGHT BIOTECHNOLOGICAL CHONDROITIN SULFATE WITH ANTI-INFLAMMATORY AND ANTIARTHRITIS ACTIVITY AND USE THEREOF IN THE PREVENTION OF OSTEOARTHRITIS

This application is a continuation-in-part of U.S. application Ser. No. 14/947,634, filed on Nov. 20, 2015, which is a continuation of U.S. application Ser. No. 14/402,646, filed on Nov. 20, 2014, which is the National Stage application under § 371 of PCT/EP2013/060471, filed on May 22, 2013, which claims priority from Italian Application No. MI2012A000880, filed on May 22, 2012, each of which is hereby incorporated by reference herein.

TECHNICAL FIELD

The present invention relates to a chondroitin sulfate (CS) with an extremely low and narrowly distributed molecular weight (1000-5000 daltons, polydispersity ranging from 1.1 to 1.3) produced by chemical sulfation of an unsulfated chondroitin backbone obtained with biotechnology techniques, and the use of said CS in the treatment and prevention of osteoarthritis and acute and chronic inflammatory processes.

BACKGROUND

Chondroitin sulfate (CS) is currently recommended by EULAR (the European League against Rheumatism) as a symptomatic slow-acting drug for osteoarthritis (SYSADOA) in the treatment of osteoarthritis of the knee (Jordan K M et al., Ann. Rheum. Dis. 62, 1145, 2003), hip (Jordan K M et al. Ann. Rheum. Dis. 62, 1145, 2003) and hand (Zhang W et al., Ann. Rheum. Dis. 66, 377, 2007) on the basis of numerous clinical findings and various meta-analyses of clinical trials. Recent clinical trials have also demonstrated that CS modifies the extracellular structures of human cartilage tissue (Reginster J Y, Heraud F, Zegels B, Bruyere O. Mini Rev Med Chem 7, 1051, 2007. Kahan A, Uebelhart D, De Vathaire F, Delmas P D, Reginster J Y. Arthritis Rheum 60, 524, 2009). CS is also widely used as a nutraceutical, either alone or combined with other ingredients (McAlindon T E et al., JAMA 283, 1469, 2000. Volpi N et al., Food Anal Meth 1, 195, 2008. Volpi N et al., Separation Sc 1, 22, 2009).

Chondroitin sulfate (CS) is a natural polysaccharide belonging to the glycosaminoglycan (GAG) class, present in both vertebrates and invertebrates, which consists of disaccharide sequences formed by alternating residues of glucuronic acid (GlcA) and N-acetyl-D-galactosamine (GalNAc) bonded to one another by beta 1-3 bonds and sulfated in different positions.

CS is present in animal tissues, with structural and physiological functions. It mainly consists of two types of disaccharide unit monosulfated at the 4- or 6-position of GalNAc (called disaccharides A and C respectively), present in different percentages depending on its origin. The CS backbone also contains non-sulfated disaccharide, generally in small amounts. Disulfated disaccharides having two sulfate groups bonded through the oxygen atom at various positions, such as the 2-position of GlcA and the 6-position of GalNAc (disaccharide D), the 2-position of GlcA and the 4-position of GalNac, or the 4- and 6-positions of GalNAc (disaccharide E), can be present in the CS backbone in variable percentages, depending on the specific animal sources (Volpi N. J. Pharm. Pharmacol. 61, 1271, 2009. Volpi N. J. Pharm. Sci. 96, 3168, 2007. Volpi N. Curr. Pharm. Des. 12, 639, 2006). The presence of sulfation at the 3-position of GlcA is possible, but in extremely small amounts; said presence is rare in CS of terrestrial origin, and more probable in the highly sulfated types of marine origin (Fongmoon D et al. J Biol Chem 282, 36895, 2007).

The formula of the repeating disaccharide unit of CS is as follows:

wherein $R_2$, $R_4$ and $R_6$ are independently H or $SO_3^-$.

The negative charges of the carboxylate and sulfate groups in the repeating disaccharide unit are generally neutralized by sodium ions.

The meanings of the acronyms most commonly used to identify the variously sulfated disaccharides are set out below:
Di-0S (R2=H; R4=H; R6=H)
Di-6S (C) (R2=H; R4=H; R6=SO3−)
Di-4S (A) (R2=H; R4=SO3−; R6=H)
Di-4,6diS (E) (R2=H; R4=SO3−; R6=SO3−)
Di-2,6diS (D) (R2=SO3−; R4=H; R6=SO3−)
Di-2,4diS (B) (R2=SO3−; R4=SO3−; R6=H)
Di-2,4,6triS (R2=SO3−; R4=SO3−; R6=SO3−)

Samples of CS originating from different animal sources are also characterized by different molecular weights and charge densities, this latter parameter being directly correlated with the specific sulfated groups.

Table 1 shows the main disaccharides found in natural CS extracted from cartilage of various animal species.

TABLE 1

| Parameters | CS Originating From Different Animal Sources | | | | | |
|---|---|---|---|---|---|---|
| | Bovine CS | Porcine CS | Chicken CS | Shark CS | Skate CS | Squid CS |
| Mn (kDa) | 12-17 | 9-14 | 8-13 | 25-40 | 27-34 | 60-80 |
| Mw (kDa) | 20-26 | 14-20 | 16-21 | 50-70 | 50-70 | 80-120 |
| Polydispersity index | 1.8-2.2 | 1.4-1.8 | 1.6-2.0 | 1.0-2.0 | 1.2-2.5 | 0.8-1.3 |
| Di-0S | 6 | 6 | 8 | 3 | 3 | 13 |
| Di-6S | 33 | 14 | 20 | 44 | 39 | 15 |
| Di-4S | 61 | 80 | 72 | 32 | 43 | 50 |
| Di-2,6diS | ND | ND | ND | 18 | 13 | 0 |
| Di-4,6diS | ND | ND | ND | 2 | 1 | 22 |

TABLE 1-continued

CS Originating From Different Animal Sources

| Parameters | Bovine CS | Porcine CS | Chicken CS | Shark CS | Skate CS | Squid CS |
| --- | --- | --- | --- | --- | --- | --- |
| Di-2,4diS | ND | ND | ND | 1 | 1 | 0 |
| Charge density | 0.90-0.96 | 0.92-0.96 | 0.90-0.94 | 1.15-1.25 | 1.08-1.20 | 1.00-1.20 |
| 4S/6S ratio | 1.50-2.00 | 4.50-7.00 | 3.00-4.00 | 0.45-0.90 | 1.00-1.40 | 2.50-4.00 |

Mn = number average molecular weight;
Mw = weight average molecular weight;
Polydispersity index = Mw/Mn;
The charge density is the number of sulfate groups per disaccharide unit;
ND = not identified The various types of CS derived from terrestrial animals have similar molecular mass parameters (Mn and Mw), whereas they differ from those of marine species, which have higher molecular mass values. CS of terrestrial origin has a mean molecular weight (Mw) between 14 and 26 kDa, whereas CS of marine origin, obtained from squid, cartilaginous fish and bony fish, has a molecular weight (Mw) exceeding 50 kDa. Terrestrial CS samples are also characterized by charge density (CD) values below 1.0, whereas marine CS samples always have CD values exceeding 1.0.

Disulfated disaccharides are usually present in trace amounts in terrestrial CS, but are more abundant in CS of marine origin. Moreover, significant amounts of polysulfated disaccharides (tri- and tetra-sulfates) are not observed in natural CS.

Natural CS also presents differences between different organs and tissues, even in the same species, as shown in Table 2.

TABLE 2

CS Derived From Different Animals and Organs/Tissues

| Parameters | Bovine cartilage | Bovine aorta | Sturgeon bones | Rabbit ileum, kidney, lung and bone marrow | Human platelets | Human plasma |
| --- | --- | --- | --- | --- | --- | --- |
| Mn (kDa) | 12-17 | ND | 25-30 | ND | ND | ND |
| Mw (kDa) | 20-26 | ND | 35-40 | ND | ND | ~15 |
| Polydispersity index | 1.8-2.2 | ND | 1.05-1.5 | ND | ND | ND |
| Di-0S | 6 | 0 | 7 | ND | 0 | 40-60 |
| Di-6S | 33 | 95-100 | 55 | ~100 | Traces | 1-5 |
| Di-4S | 61 | 0-5 | 38 | Traces | >98 | 60-40 |
| Di-2,6diS | ND | 0 | 0 | 0 | 0 | 0 |
| Di-4,6diS | ND | 0 | 0 | 0 | 0 | 0 |
| Di-2,4diS | ND | 0 | 0 | 0 | 0 | 0 |
| Charge density | 0.90-0.96 | 0.98-1.02 | 0.90-0.95 | 0.98-1.02 | 0.98-1.02 | 0.40-0.60 |
| 4S/6S ratio | 1.50-2.00 | <0.1 | 0.40-0.90 | <0.1 | >45 | 10-50 |

Mn = number average molecular weight;
Mw = weight average molecular weight;
Polydispersity index = Mw/Mn;
The charge density is the number of sulfate groups per disaccharide unit;
ND = not identified.

The existence of chains of polysaccharide or oligosaccharide CS with 100% 6-sulfate or 4-sulfate disaccharides is reported in the literature for various tissues and organs (Sampaio L. O. et al. Biol. Chem. 256, 9205, 1981; Okayama E. et al. Blood 72,745, 1988; Ambrosius M. et al. J. Chrom. A 1201, 54, 2008; Volpi N. et al. Clin. Chim. Acta 370, 196, 2006).

All these characteristics demonstrate the extreme heterogeneity of natural CS in terms of both molecular weight and charge density; however, parameters according to which a CS can be defined as "natural-like" can be identified. A chondroitin 6-sulfate which has a charge density comparable to that of CS of marine origin and is characterized by the absence of abnormal sulfation patterns presents as structurally similar to natural glycosaminoglycan. Its proven anti-inflammatory activity in vivo provides further support for the definition of natural-like CS, and supports its use in the treatment of symptoms correlated with arthritic disorders.

Many attempts have been made to find a biotechnological method for the production of CS using micro-organisms as a polysaccharide precursor source having a structure partly similar to that of CS, and then using chemical sulfation to produce a CS similar to the natural type.

Some bacteria produce capsular polysaccharides with a structure similar to glycosaminoglycans; for example, *Pasteurella multocida* produces a polysaccharide identical to non-sulfated chondroitin (De Angelis P. L., Carbohydrate Res., 337 (17), 1547, 2002). However, the *Escherichia coli* strain with serotype O5:K4:H4 produces a capsular polysaccharide with a chondroitin backbone bearing a β-fructose residue bonded at the 3-position of the GlcA unit (polysaccharide K4).

An example of production of biotechnological CS starting with capsular polysaccharide K4 from *E. coli* O5:K4:H4 is reported in EP 1304338, which describes a process wherein polysaccharide K4, produced in liquid cultures, is extracted and purified and then redissolved and subjected to acid hydrolysis to eliminate the fructose residues bonded to the GlcA residues of the polymer. The defructosylated polymer, identical to the non-sulfated backbone of CS (CH), can be sulfated at the 4- or 6-position of the GalNAc residue according to various chemical synthesis methods, to produce a CS with a molecular weight between 6 and 25 kDa. However, the biotechnological CS described in EP 1304338 is not evaluated at all for its anti-inflammatory and anti-arthritis activity, and its use in the treatment of arthritis and/or osteoarthritis remains a mere hypothesis. This is particularly important as only 70% of the polysaccharide described in EP 1304338 definitely has the structure of a natural chondroitin sulfate, the remaining 30% being mainly non-sulfated chondroitin (CH). Furthermore, oligosaccharides with a molecular weight of less than 5 kDa are not considered.

A recent publication (Bedini E. et al. Angew Chem. Int. Ed Engl. 2011) describes a process wherein the polysaccharide K4 produced is sulfated at the 4-position and/or the 6-position of the GalNAc residue in the same chain. Once again, the biotechnological CS described is not evaluated for anti-inflammatory or anti-arthritis activity, and its use in the treatment and prevention of arthritis and/or osteoarthritis and the correlated inflammatory processes is not evaluated. The same authors postulate the presence of structural modifications to the chain of biotechnological CS deriving from their synthesis process, which produces abnormal sulfation of the hydroxyl group in C3 of GlcA due to the low protection of that group during the synthesis process. This anomaly is known to cause serious toxicity in humans following intravenous administration of heparin wherein said CS 3-sulfated in GlcA was present as a contaminant. Although this toxicity has never been observed in relation to oral administration of CS, the risk of toxic effects due to that type of anomalous sulfation remains; this is also indicated by the same authors in another recent publication (Bedini, E., et al., *Chemistry: A Eur. J.* (2012) vol. 18: 2123-30).

Moreover, the biotechnological CS described by Bedini et al. (Angew Chem Int Ed Engl. 2011) has a molecular weight of around 17 kDa, and therefore potentially exhibits the low bioavailability of natural products of extraction origin. For all these reasons, the biotechnological CS described by Bedini et al. is unlikely to be used in the treatment and prevention of arthritis and/or osteoarthritis.

Examples of low-molecular-weight types of CS for use in the treatment of arthritis do exist (Cho S Y et al. Biol. Pharm. Bull. 27, 47, 2004, Das A. et al. Osteoart. Cartil. 8, 343, 2000), but they are all obtained by depolymerization of CS of animal origin, which means that the presence of viruses, prions and other transmissible infectious agents cannot be ruled out. If in vivo performance of a new low-molecular-weight CS of biotechnological origin could be shown to be different than similar low-molecular-weight CS obtained from animals, particularly in the treatment of osteoarthritis, this would represent a useful contribution to the art.

SUMMARY

The instant invention relates to a biotechnological (non-animal) CS which is substantially monosulfated, mainly at the 6-position, possesses little or no 4-sulfate, and is similar to natural CS from animals in terms of the mono/disulfated disaccharide ratio, the low level of tri-sulfated and poly-sulfated disaccharides, the charge density and the biological activity exhibited. The chondroitin sulfate (CS) according to the invention presents a lower molecular weight (1000-5000 daltons) than chondroitin sulfates extracted from animal tissues of terrestrial origin (bovine, porcine and avian, characterized by molecular weight values of 14,000-26,000 daltons) and of marine origin (shark, squid, skate and bony fish, all with a molecular weight >50,000 daltons). The molecular weight distribution of the polymer around its mean value is also very narrow, with a polydispersity of 1.1-1.3 for chondroitin sulfate of the invention.

This characteristic combination of low MW, low polydispersity and specific sulfation profile gives the product, according to the invention, better bioavailability and greater efficiency in treatment and prevention of arthritic diseases.

The use of low-molecular-weight biotechnological chondroitin sulfate (CS) in the treatment and prevention of osteoarthritis is supported by the experimental verification of its anti-inflammatory activity in a well-known animal model normally used for the study of arthritis and the associated symptoms. The low-molecular-weight biotechnological CS described also exhibits good tolerance, as demonstrated in toxicological studies conducted in accordance with the OECD guidelines for pharmaceutical products.

DETAILED DESCRIPTION

Definitions of Terms

The substances involved in this invention are cited in the previous scientific and patent literature adopting sometimes different names for the same substance: to clarify the nomenclature, in this document the following names are used.

CS: chondroitin sulfate, a polysaccharide present in various animal tissues and also used as drug or dietary supplement. Different sulfation profiles (number and position of sulfate groups within the polymer chain) are possible, depending on the animal species, tissue of origin and extraction procedure.

K4: capsular polymer present in some wild-type microorganisms, has the same chemical structure of a K4-d but decorated with fructose residues.

K4-d: capsular polymer present in recombinant microorganisms or obtained from K4 by chemical reaction, has the same chemical structure of un-sulfated chondroitin (K4-d=CH).

CH: un-sulfated chondroitin, same as K4-d can be transformed into CS by means of chemical or biological sulfation.

Description of the Embodiments

A new biotechnologically derived low-molecular-weight (LMW)-CS is described herein.

It is surprising to discover that in vivo performance of the new low-molecular-weight CS of biotechnological origin is different than similar low-molecular-weight CS obtained from animals, particularly in the treatment of osteoarthritis.

It has now been found that a chondroitin sulfate (CS) with a low molecular weight, between 1000 and 5000 daltons, or preferably between 2000 and 4000 daltons, produced by chemical sulfation of a non-sulfated chondroitin backbone obtained by biotechnological techniques, has higher anti-inflammatory activity than natural CS, improved bioavailability and a favourable safety profile. The CS described is substantially monosulfated, mainly at the 6-position, with little sulfation at the 4-position, and with a mono/disulfated disaccharide ratio and charge density similar to those of natural CS.

Except MW, the CS according to the invention presents all the characteristics of a natural CS, and more specifically of CS of marine origin. It has similar relative percentages of mono- and di-sulfated disaccharides, similar distribution of disulfated disaccharides and consequently a similar charge density (CD) associated with a low 4-sulfate/6-sulfate ratio.

The biotechnological CS according to the invention also has the following special characteristics: a very low molecular weight (between 1000 and 5000 daltons, or preferably between 2000 and 4000 daltons); a particularly high percentage of 6-sulfated disaccharides; an almost total absence of tri-sulfated disaccharides; substantial absence of sulfation at the 3-position of the GlcA residue. In particular, the presence of tri-sulfated disaccharides and disaccharides sulfated at the 3-position of GlcA characterizes the known types of synthetic CS, and often causes adverse effects in their therapeutic application. The narrow distribution around the mean MW is also a particular characteristic of the invention: it means that almost no product have a MW lower than 1 kDa or higher than 5 kDa. It is expressed by the value of polydispersity: from 1.1 to 1.3.

Table 3 shows the physicochemical characteristics of the biotechnological chondroitin sulfate according to the invention.

TABLE 3

| Physicochemical Characteristics Of Biotechnological CS | |
|---|---|
| Molecular mass (MWw) | 1000-5000 Da |
| Polydispersity | 1.1-1.3 |
| Disaccharides: | |
| Δ Di-0S | <15% |
| Δ Di-6S | ≥65% |
| Δ Di-4S | <1% |
| Δ Di-2,6diS | <20% |
| Δ Di-4,6diS | <5% |
| Δ Di-2,4diS | <1% |
| Di-sulfated total * | <13% |
| Tri-sulfated total ** | <1% |
| Charge Density | 1-1.25 |
| 4S/6S ratio | <0.1 |

\* Di-sulfated total: sum of 2,6- 2,4- and 4,6- di-sulfated disaccharides
\*\* Tri-sulfated total: sum of 2,4,6- trisulfate and any other tri-sulfated disaccharides According to a particular aspect of the invention, CS can be prepared by a chemical synthesis process applied to the polysaccharide K4-d, obtained from cultures of the *E. coli* strain DSM23644 as described in WO 2012004063: due to a mutation induced in the KfoE gene, responsible for the fructosylation of K4, this particular strain produces a polysaccharide identical to natural non-sulfated CH. After molecular weight reduction by acidic or radical depolymerization, the chondroitin is subjected to chemical sulfation as described in PCT/EP2011/058297 to give the product of this embodiment.

Alternatively, the starting non-sulfated chondroitin (CH) can be obtained from the *E. coli* strain O5:K4:H4 (WO 01/02597), that produce a fructosylated capsular polysaccharide named K4; in this example the polymer is previously defructosylated by thermoacid hydrolysis, according to known techniques (Rodriguez and Jann, Eur. J. Biochem. 117, 117-124, FEBS 1988), then, after molecular weight adjustment, the polysaccharide (a low-molecular-weight chondroitin) undergoes chemical sulfation, preferably according to the method described in PCT/EP2011/058297.

Briefly, the synthesis process that leads to sulfation of the disaccharide units is as follows:

a) The unsulfated chondroitin (CH), isolated as ammonium any of the alkaline metal salts, obtained upon defructosylation of polysaccharide K4 is desalified on cation-exchange resin and resalified with an alkylammonium hydroxide group, preferably with tetrabutylammonium hydroxide, added in a stoichiometric amount up to a pH of 7.0-7.5, and dried by freeze-drying or spray-drying.

b) The tetrabutylammonium CH salt described in step a) is added under stirring to a solution consisting of a polar aprotic solvent, preferably dimethylformamide (DMF), maintained at a temperature between 0 and 30° C.; the sulfating complex is then added in a molar ratio between 2 and 5 to the CH, maintaining a constant temperature and stirring.

c) Finally, the reaction is stopped by adding sodium bicarbonate or other base, increasing the temperature to 65° C. to evaporate off the solvent. Water is then added, followed by redistillation. The final solution is ultrafiltered and dialysed. Finally, the CS sodium salt is filtered and dried under vacuum to a residual humidity of below 10%.

If necessary, the molecular dimension of unsulfated chondroitin is reduced before the chemical sulfation by means of a controlled depolymerization process, as radical or acidic depolymerization already known in the art for chondroitin sulfate (Volpi N. et al, Carb. Res., 279, 193-200, 1995 and Cho et al, Biol Pharm Bull 27, 47-51, 2004). These processes can be carefully controlled and rapidly quenched as soon as the required medium molecular weight is reached. Due to the specific implementation of the protocol, in the present process a narrow MW distribution around the mean value is obtained: this is expressed in a low polydispersitiy index of CH obtained. The mean MW, but not the polydispersity, have a small increase during the sulfation process: as a consequence, CS with a narrow MW distribution is obtained (i.e., LMW-CS), almost all the chains are limited in the 1 kDa-5 kDa range.

As an example, acidic depolymerization is performed by suspending the CH in water, acidifying the solution with the addition of HCl to a concentration of 1 M, and heating to 60° C.

The molecular weight of the oligosaccharides generated by depolymerization is calculated by taking samples of the solution at short intervals, determining the molecular weight of the oligosaccharides by SEC-HPLC. The reaction is interrupted by neutralization with NaOH or sodium bicarbonate, so that the pH is adjusted to 6-8, when the desired molecular mass values have been reached.

Alternatively, depolymerization can be obtained by radical hydrolysis, controlling the final molecular weight of the resulting oligosaccharides as described previously. The CH is suspended in water and the pH is corrected to 7.5 by adding a 10% hydrochloric acid or sodium hydroxide solution, then a 9% solution of hydrogen peroxide ($H_2O_2$) is added and the reaction is maintained at 60° C. SEC-HPLC is performed as previously described to check whether the desired molecular weight has been reached. The reaction is interrupted by cooling the solution to room temperature (20-25° C.) and lowering the pH to 6.0.

The CS according to the invention can also be obtained by chemical sulfation according to the procedures previously indicated, using as substrate the low-molecular-weight fraction of polysaccharide K4 deriving from fermentation of *E. coli* strain O5:K4:H4. In this case, the K4 is loaded onto a gel-filtration column and separated in two fractions: a larger first pool containing high-molecular-weight K4 (40-70 kDa), almost 80% of the product, and a second pool, containing low-molecular-weight K4, with low dispersion around the mean value, between 1500 and 6000 daltons. The second pool is then subjected to the defructosylation and chemical sulfation process disclosed in PCT/EP2011/058297 until a CS with a final molecular weight limited in the 1000-5000 Dalton range is obtained.

The main fraction of high-molecular-weight polysaccharide K4 is subjected to the defructosylation, acid or radical depolymerization and finally chemical sulfation as described below, until a CS with a final molecular weight in the 1000-5000 Dalton range is obtained.

Alternatively, the low-molecular-weight biotechnological CS can be obtained by a process similar to those previously described, involving sulfation of low-molecular-weight, naturally defructosylated oligosaccharide K4-d, recovered from fermentation of *E. coli* strain DSM23644 as described in WO 2012004063. Similarly as above, the low-molecular-weight K4-d (or CH) can be obtained by fractionation, e.g. by gel filtration chromatography, and/or through a depolymerization step.

The low-molecular-weight CS thus obtained was evaluated for efficacy in an experimental animal arthritis model (Adjuvant Arthritis: AA) in the rat, and the results obtained were compared with those relating to pharmaceutical grade natural CS of extractive origin used in the same experimental model (Bauerova K. et al., Osteoarthritis Cartilage 19, 1373, 2011) after daily oral treatment with 900 mg/kg. The invention is embodied in the following examples.

For the proposed therapeutic or health uses, the CS according to the invention will be used as the active ingredient of medicaments, diet supplements or food additives, possibly combined with other active ingredients such as glucosamine hydrochloride, glucosamine sulfate, N-acetyl glucosamine, methyl-sulphonylmethane (MSM), vitamin K, vitamin D, group B vitamins, folates, reduced folates, hyaluronic acid, amino acids, collagen, hydrolysed collagen, polyunsaturated fatty acids, keratin, dermatin, S-adenosylmethionine (SAMe), ascorbic acid or manganese ascorbate.

Examples of formulations according to the invention include capsules, soft gel capsules, tablets, drinks in liquid form, and powdered drinks to be reconstituted.

The doses of the CS according to the invention will be between 100 and 3000 mg/day, preferably between 100 and 2000 mg/day, more preferably between 150 and 750 mg/day, and most preferably between about 150 mg/day and about 600 mg/day. For example, the daily dose for a human individual in need of treatment for an inflammatory condition such as osteoarthritis can be in a range of about 150 mg/day and about 600 mg/day.

The method of preparing and characterizing a low polydispersity, low molecular weight biotechnological chondroitin sulfate and the use of said CS in the treatment and prevention of osteoarthritis and acute and chronic inflammatory processes may be further understood in connection with the following Examples and embodiments. In addition, the following non-limiting Examples and embodiments are provided to illustrate the invention.

Example 1. Preparation of Low-Molecular Weight CS from Low-Molecular-Weight K4

The CS according to this embodiment can be obtained by chemical sulfation according to the procedures previously indicated, using as substrate the low-molecular-weight fraction of polysaccharide K4 deriving from fermentation of *E. coli* strain O5:K4:H4. Cultivation of wild-type *Escherichia coli* strain is conducted as described in EP1304338. At the end of fermentation the culture broth is treated by heating at 80° C. for 60 minutes to deactivate the micro-organism, and is then centrifuged and ultrafiltered as in EP 1304338. The resulting supernatant is then loaded onto a gel-filtration column and the fractions are collected, checking the uronic acid content of each one to detect the presence of K4. By combining the fractions that test positive to the uronic acid test, two separate pools can be isolated: a first pool containing high-molecular-weight K4 (40-70 kDa), corresponding to the known polysaccharide and quantitatively corresponding to 80% of the total saccharides, and a second pool, clearly separated from the first on the basis of the elution volume and containing low-molecular-weight K4, with low dispersion around the mean value, between 1500 and 6000 daltons. The identity of the oligosaccharides contained in said second low-molecular-weight pool with K4 is demonstrated by the simultaneous positive response to the uronic acid assay and digestibility with chondroitinase ABC, accompanied by the appearance of disaccharide units.

Said fraction of oligosaccharide K4, which quantitatively represents 20% of the total saccharides, is then subjected to the acid defructosylation (as described in Example 2 below), thus obtaining a LMW-CH, and finally to chemical sulfation process (as disclosed in PCT/EP2011/058297) until a CS with a final molecular weight in the 1000-5000 Dalton range is obtained. See Table 3 above for sulfation profile and other product specifications.

The main fraction of high-molecular-weight polysaccharide K4 is subjected to the defructosylation, acid or radical depolymerization and finally chemical sulfation as described in the examples below, until a CS with a final molecular weight in the 1000-5000 Dalton range is obtained.

Example 2. Preparation of Low-Molecular Weight CS from Natural K4-d

Cultivation of *Escherichia coli* strain DSM23644 is conducted as described in PCT/EP2011/059069, Example 3; at the end of fermentation the biomass is separated by means of centrifugation. The supernatant is then concentrated by means of ultrafiltration with polysulphone membrane at 30 kDa (molecular weight cut-off); low-molecular weight substances from fermentation as inorganic salts, amino acids, small polypeptides and polysaccharides are eliminated in permeate, while the desired product is retained in the retentate. It consist in an acqueous solution of un-fructosylated, un-sulfated chondroitin polymer (K4-d) having a high molecular weight, approximately more than 40-50 kDa. The solution is then subjected to acid hydrolysis by adding hydrochloric acid until a final concentration of 0.5 N and incubating at +60-80° C. The molecular weight distribution is monitored at time intervals by HPLC-SEC analysis, carried out on two 5 μm Agilent Bio Series SEC©-5 (hydrophilic neutral polymeric monolayer) columns of 300 and 150 Å respectively, in series.

Table 4 shows the molecular weight values typical of an oligosaccharide analyzed with SEC-HPLC during the reaction steps until the end of depolymerization.

TABLE 4

Representative Time Profile of Molecule Weight of Oligosaccharide in Depolymerization Reaction.

| Time (minutes) | MWw (kDa) | Polydispersity Index | Relative MWw (% of initial value) |
|---|---|---|---|
| 0 | 77.3 | 1.2 | 100.0 |
| 60 | 73.6 | 1.2 | 95.3 |
| 120 | 81.9 | 1.2 | 106.0 |
| 180 | 76.3 | 1.3 | 98.7 |
| 330 | 45.7 | 1.4 | 59.1 |
| 390 | 39.7 | 1.4 | 51.4 |
| 510 | 28.6 | 1.5 | 37.0 |
| 660 | 25.5 | 1.6 | 33.0 |
| 780 | 20.5 | 1.6 | 26.5 |
| 840 | 18.7 | 1.6 | 24.2 |
| 900 | 18.1 | 1.6 | 23.4 |
| 1020 | 14.0 | 1.6 | 18.1 |
| 1200 | 10.2 | 1.6 | 13.2 |
| 1440 | 3.7 | 1.6 | 9.96 |

Once the mean MW is below 10 kDa, the depolymerization reaction is quenched by adding sodium hydroxide until neutralization (pH 6 to 8) and cooling to ambient temperature. The low-molecular weight chondroitin is concentrated and purified by means of ultrafiltration and dialysis on a polysulfone membrane at 5 kDa MWCO: sodium chloride and very-low molecular weight substances (mainly mono- and di-saccharides) are eliminated in the permeate. The solution is further purified and decolored by filtration on charcoal, then product is isolated by precipitation adding isopropanol as anti-solvent, filtered and washed with isopropanol, dried under vacuum.

The solid un-sulfated chondroitin (Na salt) is dissolved in pure water at 40 g/l and subjected to treatment with ion-exchange resin Amberjet 1200H (Rohm & Haas) in acid form, as described in PCT/EP2011/058297, Example 1. The product is recovered from the resin and salificated with tetrabuthylammonium hydroxide, the resulting CH-TBA salt solution is then desiccated in a spray-dry to obtain the product in solid and dry form.

Low-molecular weight chondroitin tetrabuthylammonium salt if further desiccated in a static dryer at 105° C. until reach a residual moisture lower than 0.2% (Karl-Fisher titration) before use in the sulfation reaction.

Sulfation is performed in anhydrous DMF employing the sulphur trioxide-pyridine complex as described in PCT/EP2011/058297, Example 3; after quenching, the solution is subjected to ultrafiltration and dialysis as described therein.

Low-molecular-weight chondroitin sulfate sodium salt is isolated as a pure and almost-white solid by spray-dry desiccation; the product matches specification of Table 3 above.

Example 3. Preparation of Low-Molecular Weight CS from K4-d

*E. coli* fermentation and chondroitin (K4-d) purification are made as described in Example 2 above, but the molecular weight reduction step is conducted following the radical depolymerization protocol with cupper acetate and hydrogen peroxide previously described by Volpi on heparin (J Chromatogr, 1993) and applied to chondroitin sulfate by Cho (Biol Pharm Bull, 2004). At the end of reaction, the product is subjected to ultrafiltration as described above, then to a cupper removal step by means of Chelex 100 chelating resin as described by Volpi.

The LMW-CH Na salt is not isolated in solid form but the solution is directly treated with Amberjet 1200H as described above, then the product is obtained by spray-dry desiccation as LMW-CH TBA salt. The solid is further desiccated under vacuum until reach a residual moisture lower than 0.5% (K-F).

Chemical sulfation is made as described in PCT/EP2011/058297, Example 4 and final product is described in Table 3 above.

Example 4. Preparation of Low-Molecular Weight CS from K4

Fermentation of *E. coli* O5:K4:H4 strain was conducted as described by Rodriguez et al Eur. J. Biochem, 177, 117-124, (1988); this wild-type strain produces a capsular polysaccharide named K4 having the same structure as a chondroitin but decorated with fructose residues. The product is then completely defructosylated by acid hydrolysis at pH 2.8, as described in the same article, thus obtaining a high-molecular-weight (un-sulfated) chondroitin (or K4-d); the acid hydrolysis is then pushed to obtain depolymerization to give LMW-CH, by simple warming the acqueous solution to +60-80° C. The depolymerization reaction is monitored by HPLC-SEC as described in Example 1 above and interrupted by neutralization (with NaOH) and cooling. By this way, fructose removal and MW adjustment are performed in a one-pot reaction scheme.

Example 5. Depolymerization of Animal Chondroitin Sulfate—Cho's Method

Commercial chondroitin sulfate from shark cartilage is subjected to acid depolymerization adopting the protocol described by Cho et al in Biol. Pharm Bull 27, 47-51, 2004. The reaction was continuously monitored and quenched when the desired MW (around 3.000) was reached.

Animal derived CS dispersity ranges depending on the animal source (i.e 1.8-2.2 Bovine CS or 1.2-2.5 for Skate CS, etc.) and it tends to increase (i.e more disperse polymer) during depolymerization.

When a sample of high molecular weight (HMW) chondroitin sulfate is subjected to chemical depolymerization according to Cho (acid or radical), due to attack at random positions, an increase in the polydispersity index is observed (see Table 5).

TABLE 5

Polydispersity Index of Animal Derived CS (Cho's Method)

| Batch no: | Sample: | Molecular Weight ESTD $MW_W$ kDa: | PDI SLS $MW_W/MW_N$ |
| --- | --- | --- | --- |
| 22M17DS | Time0 | 17.6 | N/A |
| | Log 1 | 14.5 | N/A |
| | Log 2 | 9.7 | N/A |
| | Log 3 | 7.7 | 1.4 |
| | Log 4 | 3.5 | 1.8 |
| | Anti-solvent precipitation | 3.7 | 1.7 |

PDI = polydispersity

Even a further product precipitation by anti-solvent addition, as suggested by Cho, does not significantly improve the dispersity, that remains higher than the biotechnological CS described in the examples above.

Example 6. Induction of Arthritis (Adjuvant Arthritis, AA) in Rats, and Treatment with the Low-Molecular-Weight Chondroitin Sulfate (LMW-CS) of the Invention AA was induced by a single intradermal injection of *Mycobacterium butyricum* in incomplete Freund's adjuvant. The study involved one group of healthy animals (HC), one group of untreated arthritic animals (AC) and two groups of arthritic animals treated with two different regimens. The first treatment regimen involved pre-treatment consisting of administration of 900 mg/kg of biotechnological CS a day for 14 days before arthritis was induced, continuing for 28 days after the induction of AA (PT). The second treatment regimen involved the administration of 900 mg/kg of biotechnological CS a day only during the 28 days after induction of AA (T).

Figure 1:
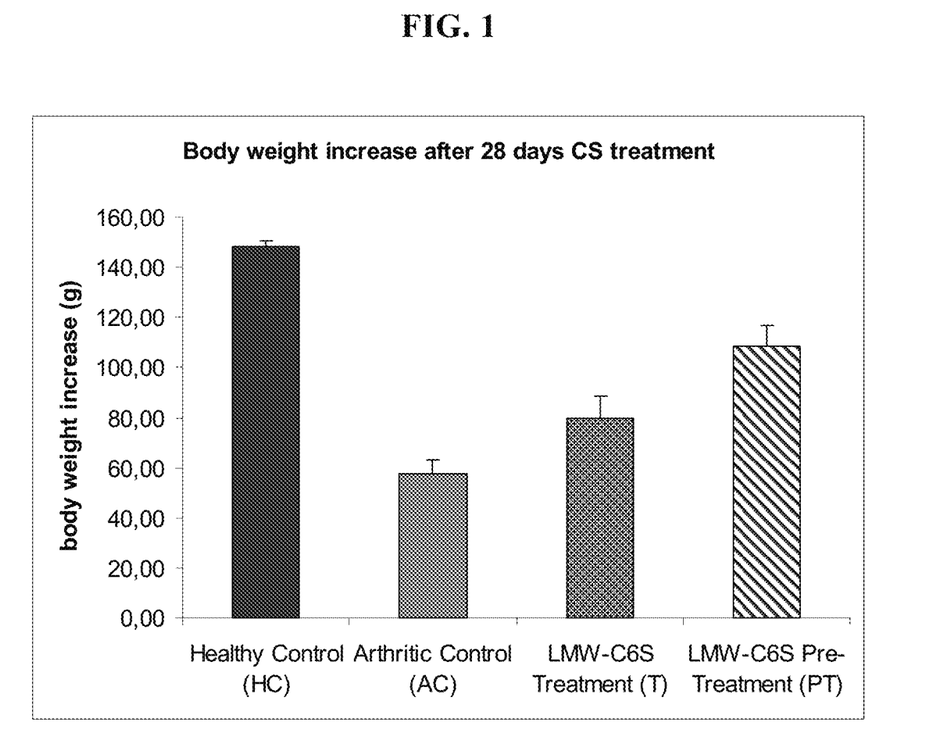
FIG. 1 illustrates, in one embodiment, increase in body weight of rats suffering from Adjuvant Arthritis (AA) following treatment with low-molecular-weight biotechnological CS. Key: HC, healthy control; AC, arthritic control; T, group treated with CS (days 0 to 28); PT, group pre-treated with CS (days −14 to 28). Values expressed in g±SEM.

The physiological increase in body weight of the rats was very low in the untreated arthritic animals (AC), amounting to about 40% of that of the healthy controls at the end of the study. Pre-treatment with biotechnological CS (PT group) limited this reduction: the increase in body weight amounted to 73% of that of the healthy controls. The treatment alone (T) also proved effective in restoring body weight, though to a lesser extent (an increase of 54% compared with the healthy controls) (FIG. 1). This is attributable to the anti-inflammatory role of low-molecular-weight biotechnological CS at systemic level. This effect on the increase in body weight of the animals is higher than that found in the study by Bauerova et al., conducted with a high-molecular-weight CS of bovine origin at the same dose (Bauerova K. Et al., Osteoarthritis Cartilage 19, 1373, 2011). This finding confirms the greater intestinal absorption of the biotechnological CS according to the invention.

Figure 2:
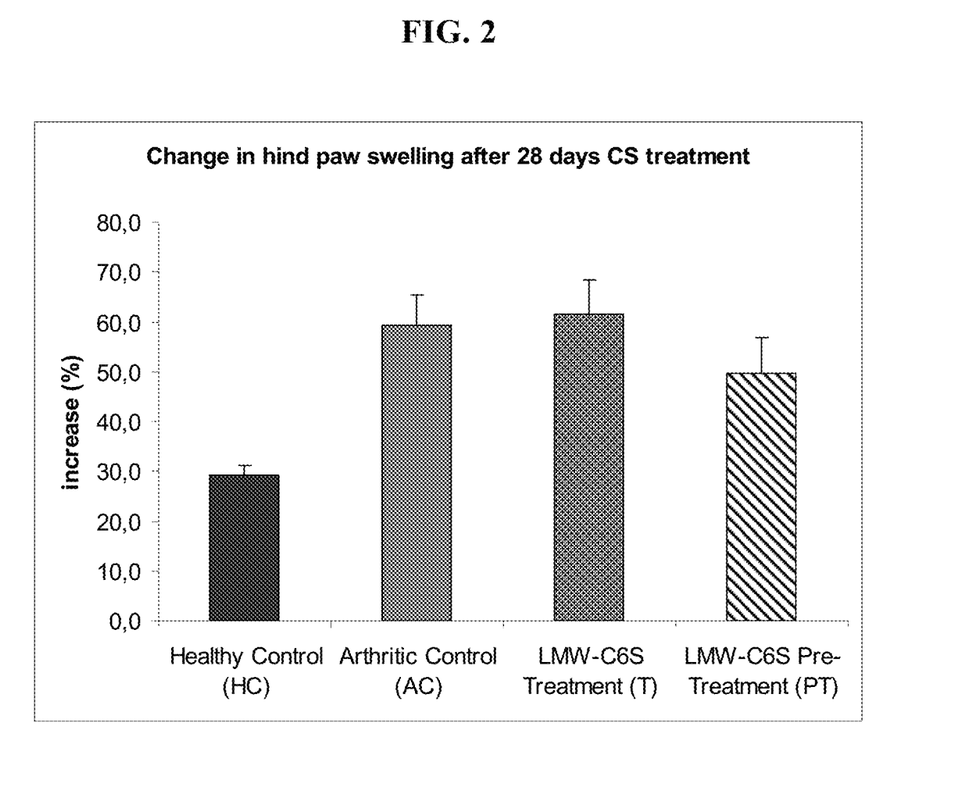
FIG. 2 illustrates, in one embodiment, evaluation of oedema in the hind limbs of rats suffering from Adjuvant Arthritis (AA) following treatment with low-molecular-weight biotechnological CS. Key: HC, healthy control; AC, arthritic control; T, group treated with CS (days 0-28); PT, group pre-treated with CS (days −14 to 28). Percentage increase: measurement effected as increase in volume (ml), calculation of percentage: $[(Day_n/Day_0) \times 100]-100$ Values expressed as %±SEM.
Figure 3:
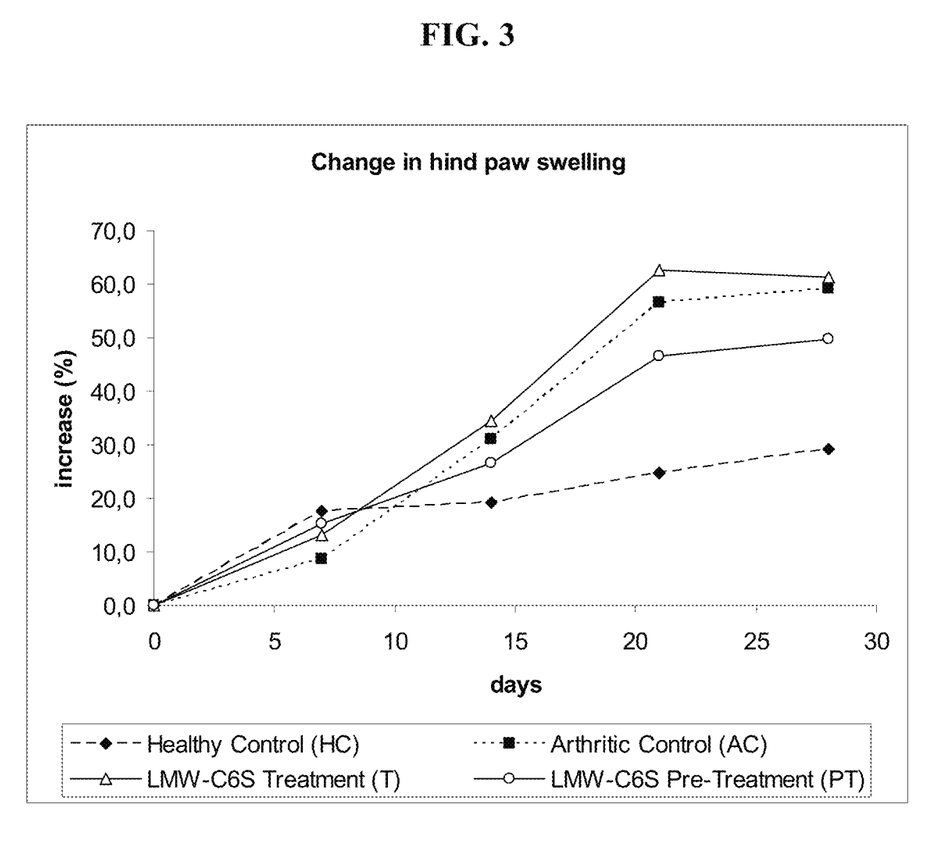
FIG. 3 illustrates, in one embodiment, progression of oedematous state during study in rats suffering from Adjuvant Arthritis (AA) following treatment with low-molecular-weight biotechnological CS. Key: HC, healthy control; AC, arthritic control; T, group treated with CS (days 0-28); PT, group pre-treated with CS (days −14 to 28). Evaluation of percentage increase in volume 0, 7, 14, 21 and 28 days after induction of AA. Values expressed as percentile.

The severity of the arthritis was quantified on the basis of the increasing levels of swelling of the limbs (oedema); the oedema that developed in the hind paw was significantly reduced in the pre-treated animals (PT) (FIG. 2). Pre-treatment with biotechnological CS significantly reduced oedema throughout the study compared with the untreated controls (FIG. 3).

Figure 4:
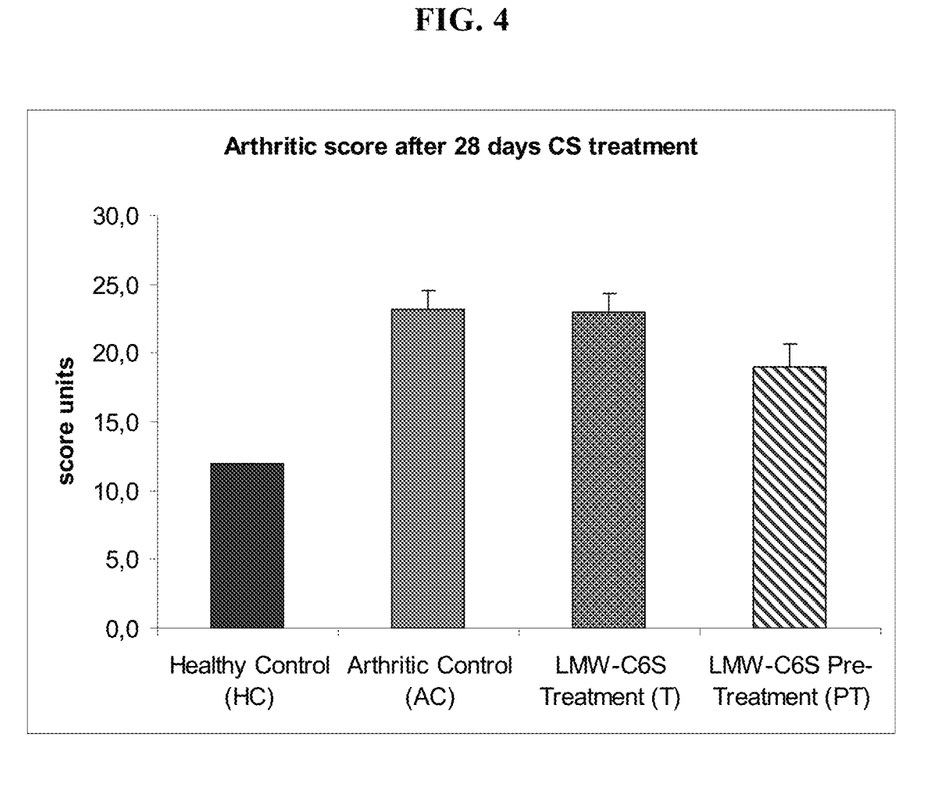
FIG. 4 illustrates, in one embodiment, arthritis score in rats suffering from Adjuvant Arthritis (AA) following treatment with low-molecular-weight biotechnological CS. Key: HC, healthy control; AC, arthritic control; T, group treated with CS (days 0-28); PT, group pre-treated with CS (days −14 to 28). Score: periarticular swelling and erythema of forepaws (1-5), periarticular swelling and erythema of hind paws (1-8), diameter of scab at base of tail (1-5). Values expressed in units±SEM.
Figure 5:
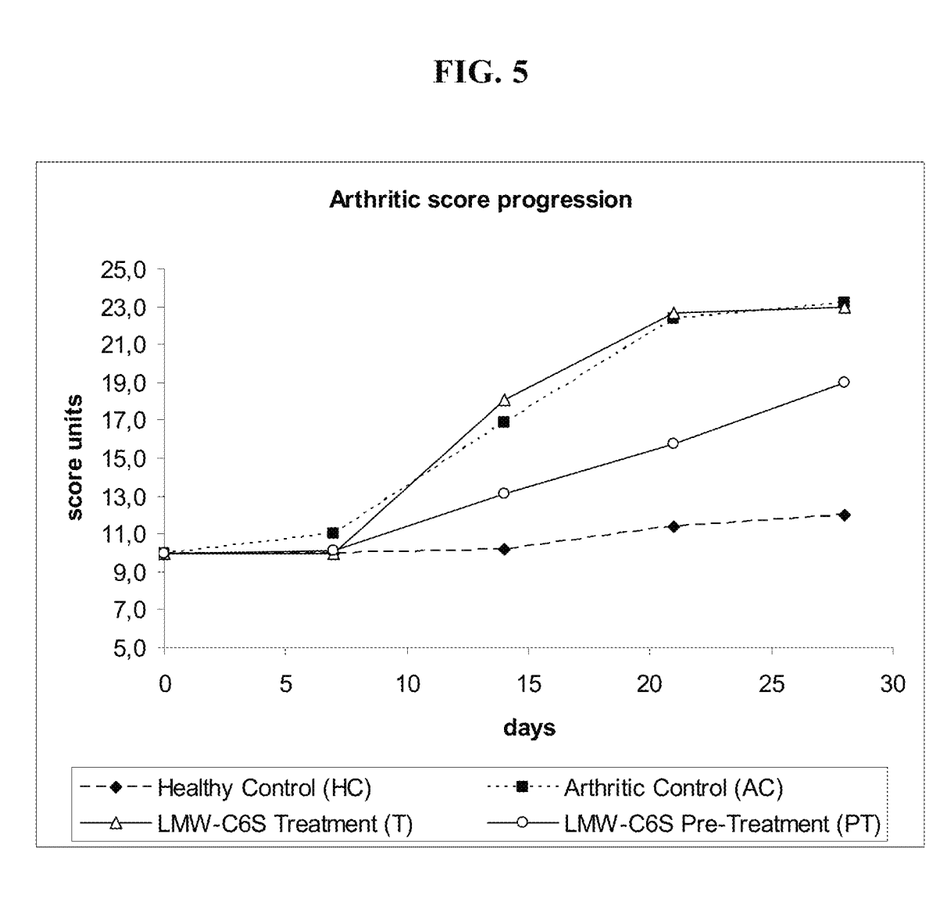
FIG. 5 illustrates, in one embodiment, progression of arthritis score during study in rats suffering from Adjuvant Arthritis (AA) following treatment with low-molecular-weight biotechnological CS. Key: HC, healthy control; AC, arthritic control; T, group treated with CS (days 0-28); PT, group pre-treated with CS (days −14 to 28). Evaluation of scores: 0, 7, 14, 21 and 28 days after induction of AA. Values expressed in units.

The pre-treatment also proved effective in reducing the total arthritis score, a parameter which takes account of a set of clinical factors comprising periarticular erythema, developed oedema and the diameter of the scab at the adjuvant injection site at the base of the tail. The arthritis evaluation scale allocates a score between 6 and 31; the arthritis control group (AC) obtained a value of 23, whereas the PT group reached a value of 19, as against 12 for the healthy controls (HC) (FIG. 4). Moreover, the pre-treatment proved effective throughout the subacute phase, from day 1 to day 28 after induction of AA (FIG. 5). The treatment-only (T) group did not significantly influence the arthritis score during the study period.

Example 7. Induction of Arthritis (Adjuvant Arthritis, AA) in Rats, and Treatment with Low-Molecular-Weight Biotechnological CS (LMW-CS)

40 male Lewis rats weighing between 150 and 190 g were divided at random into four groups of 10 animals each, housed in polypropylene cages in an environment maintained at the temperature of 22±2° C., and fed on a standard laboratory diet with unlimited access to water.

The experimental groups were as follows:
1) An untreated healthy control group (HC).
2) An untreated control group with adjuvant-induced arthritis (AC).
3) A group of arthritic rats orally treated with biotechnological CS at the dose of 900 mg/day per kg of body weight for 28 days after induction of AA (days 0-28 of the experiment) (T).
4) A group orally pre-treated with biotechnological CS at the dose of 900 mg/day per kg of body weight for 14 days preceding the induction of AA, and for the 28 days after induction of AA (days −14 to 28 of the experiment) (PT).

Arthritis was experimentally induced in the rats on day 0 by a single intradermal injection at the base of the tail of 1 ml of a mixture consisting of *Mycobacterium butyricum* inactivated by heat in incomplete Freund's adjuvant.

The CS of the invention was dissolved in distilled water at the concentration of 20 mg/ml and administered orally as a single daily dose by gavage.

Example 8. Effects of Biotechnological CS on the Assessment of AA in Rats by Monitoring Body Weight The body weight of the rats was measured before induction of AA (day 0), on days 7, 14 and 21, and at the end of the treatment (day 28). The effect of the treatment on this parameter was evaluated by comparing the weight increases of the different groups during the treatment period. The values found are reported in Table 6.

TABLE 6

Effects of Biotechnological CS on Body Weight of Rats with AA

| | Change in body weight: $\Delta(day_n - day_0)$ | | | | |
|---|---|---|---|---|---|
| Day ($day_n$) | 0 | 7 | 14 | 21 | 28 |
| Healthy Control (HC) | 0.0 | 98.19 | 120.93 | 135.37 | 148.33 |
| SEM | 0.0 | 1.76 | 2.01 | 1.99 | 2.47 |
| Arthritic Control (AC) | 0.0 | 74.73 | 76.77 | 51.93 | 57.57 |
| SEM | 0.0 | 4.06 | 7.02 | 6.05 | 5.71 |
| LMW-CS Treatment (T) | 0.0 | 85.19 | 89.19 | 68.39 | 79.78 |
| SEM | 0.0 | 3.03 | 5.63 | 7.52 | 8.86 |
| LMW-CS Pre-Treatment (PT) | 0.0 | 92.96 | 107.26 | 93.39 | 108.63 |
| SEM | 0.0 | 2.94 | 6.48 | 8.65 | 8.29 |

SEM: Standard Error of the Mean

Example 9. Effects of Biotechnological CS on the Assessment of AA in Rats by Monitoring the Oedema Developed The oedema that developed as a consequence of arthritis was measured by observing the increase in volume of the hind paw with a caliper suitable for the measurement. The measurements were performed before the induction of AA (day 0) and on days 7, 14, 21 and 28 of the study.

The data were expressed as the percentage increase in oedema calculated with the following formula: $[(Day_n/Day_0) \times 100] - 100$, $Day_0$ being the measurement on the initial day and $Day_n$ the measurement on the day considered. The values found are reported in Table 7.

TABLE 7

Effects of Biotechnological CS on Oedema of Rats with AA

| | Change in hind paw swelling: $[(Day_n/Day_0) \times 100] - 100$ (%) | | | | |
|---|---|---|---|---|---|
| Day ($day_n$) | 0 | 7 | 14 | 21 | 28 |
| Healthy Control (HC) | 0.0 | 17.6 | 19.3 | 24.8 | 29.1 |
| SEM | 0.0 | 1.5 | 1.4 | 1.8 | 2.0 |
| Arthritic Control (AC) | 0.0 | 8.6 | 31.0 | 56.7 | 59.3 |
| SEM | 0.0 | 1.2 | 4.6 | 6.5 | 6.1 |
| LMW-CS Treatment (T) | 0.0 | 13.1 | 34.5 | 62.8 | 61.4 |
| SEM | 0.0 | 1.0 | 6.4 | 8.1 | 7.1 |
| LMW-CS Pre-Treatment (PT) | 0.0 | 15.4 | 26.7 | 46.5 | 49.7 |
| SEM | 0.0 | 1.5 | 4.9 | 6.9 | 7.1 |

SEM: Standard Error of the Mean

Example 10. Effects of Biotechnological CS on the Assessment of AA in Rats by Monitoring the Arthritis Score The arthritis score was evaluated by allocating a score to the observation of paw joint swelling (oedema), the extent of periarticular erythema and the diameter of the scab at the adjuvant injection site at the base of the tail. The arthritis score or arthrogram was measured as the sum total of oedema (in ml, score 1 to 8), plus the diameter of the forepaw (in mm, max score 1 to 5), plus the diameter of the scab at the site of application of *Mycobacterium butyricum* measured parallel to the spinal column (in mm, max score 1 to 5), for each animal. The values found are reported in Table 8.

TABLE 8

Effects of Biotechnological CS on Arthritis Score of Rats with AA

| | Arthritis score: | | | | |
|---|---|---|---|---|---|
| Day ($day_n$) | 0 | 7 | 14 | 21 | 28 |
| Healthy Control (HC) | 10.0 | 10.0 | 10.2 | 11.4 | 12.0 |
| SEM | 0.0 | 0.0 | 0.1 | 0.3 | 0.0 |
| Arthritic Control (AC) | 10.0 | 11.0 | 16.9 | 22.4 | 23.2 |
| SEM | 0.0 | 0.4 | 1.2 | 1.4 | 1.3 |
| LMW-CS Treatment (T) | 10.0 | 10.0 | 18.1 | 22.7 | 23.0 |
| SEM | 0.0 | 0.0 | 1.7 | 1.9 | 1.3 |
| LMW-CS Pre-Treatment (PT) | 10.0 | 10.1 | 13.1 | 15.8 | 19.0 |
| SEM | 0.0 | 0.1 | 0.8 | 1.3 | 1.7 |

SEM: Standard Error of the Mean

Example 11. Safety Evaluation of Low-Molecular-Weight Biotechnological CS

The CS according to the invention was also tested for its toxicological safety in animals and on cell cultures according to various protocols designed to assess its potential genotoxicity at cell level and acute oral toxicity in the rat. All the tests used were validated and conducted according to OECD guidelines for pharmaceutical products.

The biotechnological CS was subjected to mutagenesis tests in bacterial cells (bacterial reverse mutation, Ref. OECD 471) which tested the ability of the product to induce the appearance of reverse mutants in auxotrophic strains of *E. coli* and *Salmonella typhimurium*. No significant increase in bacterial mutagenicity was observed.

The genotoxicity of biotechnological CS was also examined in two other tests on eukaryotic cell cultures, namely the test for chromosome aberrations in Chinese hamster ovary cells in vitro, OECD Ref. 473) and a mutagenicity test on murine lymphoma cells (Mutation in L5178Y $TK^{+/+}$ mouse lymphoma cells, Prot. OECD 476). No significant increase in genetic toxicity was found in the two studies cited up to the highest CS concentration used (5000 μg/plate and 5000 μg/ml respectively).

Finally, acute toxicity after oral administration was examined in Sprague-Dawley rats up to the dose of 2000 mg/kg of body weight. After observation lasting 14 days after the administration, the rats did not show any clinical signs of suffering, and no mortality occurred. Moreover, the autopsy performed at the end of the study did not indicate any signs of toxicity in the tissues and organs examined.

Example 12. Comparative Effects of Biotechnological CS vs. Animal CS on the Assessment of AA in Rats by Monitoring the Arthritis Score In order to further demonstrate the peculiar activity of biotechnological LMW-CS of the present invention, its effect in the AA model in rats was compared with a similar LMW-CS obtained from animal source (e.g. shark). As described in Example 5, commercial (high-molecular-weight) chondroitin sulfate material was subjected to depolymerization according to Cho, under controlled condition, until the desired mean MW was reached.

The product of Example 5 was tested in vivo vs. biotechnological chondroitin of the invention obtained as described in Ex. 4 (equivalent to the product obtained from any of the Examples 1, 2 or 3).

Figure 6:
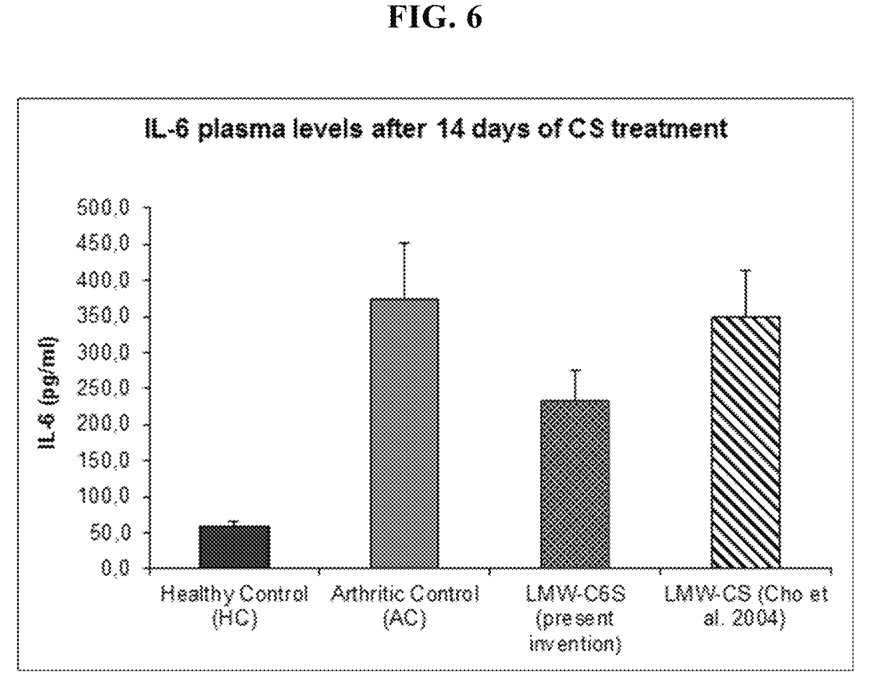
FIG. 6 illustrates, in one embodiment, interleukine-6 levels in plasma after 14 days of treatment. Comparative example: performance of low-molecular-weight CS from animal origin vs. the low-molecular-weight CS of the invention in the treatment of inflammation related to experimental osteoarthritis in rats.
Figure 7:
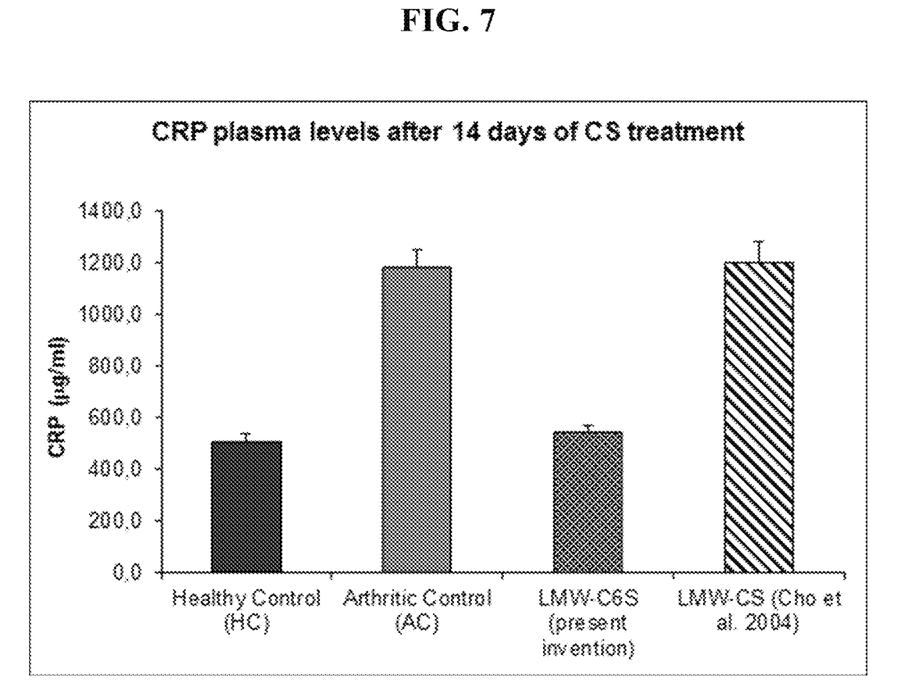
FIG. 7 illustrates, in one embodiment, C-reactive protein levels in plasma after 14 days of treatment. Comparative example: performance of low-molecular-weight CS from animal origin vs. the low-molecular-weight CS of the invention in the treatment of inflammation related to experimental osteoarthritis in rats.

Two key parameters were analyzed to determine the efficacy of the treatment in reducing the inflammation related to osteoarthritis: C reactive protein (CRP) and interleukin-6 (IL-6) plasma levels. IL-6 is a major pro-inflammatory cytokine and its level significantly increases in arthritic rats. CRP is another important marker for systemic inflammation, its plasmatic level rises up during arthritis progression. AA was induced in male Lewis rats with a single intradermal injection of heat-inactivated *Mycobacterium butyricum* in incomplete Freund's adjuvant. The following anti-osteoarthritic treatment consisted in daily oral (900 mg/kg b.w.) administrations of LMW-CS starting from day 0, i.e. the day of bacterial inoculation. The results are reported in the tables and figures herein (Tables 9-10 and FIGS. 6-7) and show that, for both parameters, LMW-CS of the present invention is efficacious after a period of 14 days of treatment while the analogous LMW-CS obtained from animal source is not. In fact, both CRP (FIG. 7) and IL-6 plasma (FIG. 6) levels decreased after the treatment with biotechnological LMW-CS, while were not or little affected by the treatment with animal LMW-CS.

TABLE 9

Efficacy of Biotech LMWCS in the AA Rat Model vs. LMW-CS According to Cho et al. 2004 - IL-6 Plasma Levels

| Day ($day_n$) | IL-6 plasma levels (pg/ml) 14 |
|---|---|
| Healthy Control (HC) | 58.3 |
| SEM | 7.6 |
| Arthritic Control (AC) | 374.1 |
| SEM | 78.5 |
| LMW-C6S (present invention) | 233.9 |
| SEM | 40.8 |
| LMW-CS (Cho et al. 2004) | 348.2 |
| SEM | 66.1 |

TABLE 10

Efficacy of Biotech LMWCS in the AA Rat Model vs. Animal LMW-CS - C-Reactive Protein (CRP) Plasma Levels

| Day ($day_n$) | CRP plasma levels (μg/ml) 14 |
|---|---|
| Healthy Control (HC) | 505.6 |
| SEM | 32.3 |
| Arthritic Control (AC) | 1184.8 |
| SEM | 68.8 |
| LMW-C6S (present invention) | 548.8 |
| SEM | 24.2 |
| LMW-CS (Cho et al. 2004) | 1202.0 |
| SEM | 83.2 |

These results confirm that biotechnological LMW-CS of the present invention and LMW-CS obtained (according to Cho) from animal source are different entities having a different biological activity as exerted in the same animal models and for the same pathology. It is still not clear why the two products, with similar sulfation profile and the same mean molecular weight, performs differently in the AA models in rats. As first hypothesis, this difference can be attributed to the presence of CS-like biologically active impurities present in animal CS, as dermatan sulfates, hyaluronic acid and keratan sulfates. While biotechnological LMW-CS is highly pure and standardized to avoid the presence of other molecules and macromolecules, animal chondroitin is obtained from food waste materials and only roughly purified, the presence of other macromolecules besides CS is possible. Beside, CS purified from animal tissues always shows a large polydispersity index concerning its mean molecular weight, due to the animal nature of this polysaccharide, ranging from 1.35 to 3.10. When depolymerized, due to the random degradation of the polysaccharidic chains, the LMW-CS produced has an even broader polydispersity index, greater than the original material. On the contrary, biotechnological LMWCS always shows a very low polydispersity index, ranging from 1.2 to 1.6, according to Table 4. The narrow-range MW distribution of LMW-CS is probably responsible for its better absorption and higher biological activity.

Oral formulations of LMW-CS are contemplated. Useful therapeutic dosages of LMW-CS can range, but are not limited to, from about 1 mg to about 5000 mg in a human individual. Another suitable dose range is from about 5 mg to about 500 mg. Another suitable dose range is from about 50 mg to about 500 mg. LMW-CS may be formulated orally as a pharmaceutical or nutraceutical composition, including a pharmaceutically or nutraceutically acceptable excipient, respectively. In one embodiment of a pharmaceutical composition containing LMW-CS, a suitable level of LMW-CS may range from about 0.01% by weight to about 50% by weight, based on the total weight of the composition. In another embodiment of a pharmaceutical composition containing LMW-CS, a suitable level of LMW-CS may range from about 0.1% by weight to about 10% by weight, based on the total weight of the composition.

The pharmaceutical compositions of the present invention may be administered in combination with a pharmaceutically or nutraceutically acceptable carrier. The active ingredients in such formulations may comprise from 1% by weight to 99% by weight, or alternatively, 0.1% by weight to 99.9% by weight. "Pharmaceutically or nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The embodiments disclosed herein are not intended to be exhaustive or to be limiting. A skilled artisan would acknowledge that other embodiments or modifications to instant embodiments can be made without departing from the spirit or scope of the invention. The aspects of the present disclosure, as generally described herein and illustrated in the figures, can be arranged, substituted, combined, separated, and designed in a wide variety of different configurations, all of which are contemplated herein.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

We claim:

1. A biotechnological chondroitin sulfate comprising:
   6-monosulfate disaccharides in an amount equal to or greater than 65% by weight;
   4-monosulfate disaccharides in an amount less than about 1% by weight;
   2,6-disulfate disaccharides in an amount less than or equal to 20% by weight;
   4,6-disulfate disaccharides in an amount less than about 5% by weight;
   2,4-disulfate disaccharides in an amount less than about 1% by weight;
   trisulfated disaccharides in an amount less than about 1% by weight;
   non-sulfated disaccharides in an amount less than about 15% by weight;
   a charge density value ranging from about 1 to about 1.25; and
   a polydispersity index ranging from about 1.1 to about 1.3;
   wherein the molecular weight (Mw) of the chondroitin sulfate ranges from 1000 to 5000 daltons.

2. The chondroitin sulfate of claim 1, wherein the chondroitin sulfate is obtained by chemical sulfation of low-molecular-weight chondroitin or capsular polysaccharide K4-d obtained from fermentation.

3. The chondroitin sulfate of claim 2, wherein the chondroitin is obtained by removal of the fructose residues of polysaccharide K4 of *E. coli* by means of hydrolysis.

4. The chondroitin sulfate of claim 2, wherein the low-molecular-weight chondroitin is obtained by acid or radical depolymerization of the polysaccharide K4.

5. The chondroitin sulfate of claim 2, wherein the low-molecular-weight chondroitin is obtained by acid or radical depolymerization of the polysaccharide K4-d.

6. The chondroitin sulfate of claim 1, wherein the chondroitin sulfate is obtained by acid or radical depolymerization of the capsular polysaccharide originally free from fructose residues (K4-d) produced by the *E. coli* strain DSM23644 and subsequent chemical sulfation.

7. The chondroitin sulfate of claim 1, wherein the chondroitin sulfate is obtained by chemical sulfation of the low-molecular-weight fraction of capsular polysaccharide originally free from fructose residues (K4-d) produced by the *E. coli* strain DSM23644.

8. The chondroitin sulfate of claim 7, wherein the removal of fructose from polysaccharide K4-d and the depolymerization are obtained in a single one-pot step.

9. The chondroitin sulfate of claim 6, wherein the removal of fructose from polysaccharide K4-d and the depolymerization are obtained in a single one-pot step.

10. The chondroitin sulfate of claim 5, wherein the removal of fructose from polysaccharide K4-d and the depolymerization are obtained in a single one-pot step.

11. The chondroitin sulfate of claim 4, wherein the removal of fructose from polysaccharide K4-d and the depolymerization are obtained in a single one-pot step.

12. The chondroitin sulfate of claim 3, wherein the removal of fructose from polysaccharide K4-d and, the depolymerization are obtained in a single one-pot step.

13. A method of treating or preventing acute or chronic inflammatory conditions in humans or animals comprising administering to the humans or animals in need thereof the chondroitin sulfate of claim 1.

14. The method of claim 13, wherein the inflammatory condition is osteoarthritis.

15. The method of claim 14, wherein the chondroitin sulfate is administered in a daily dose of from about 150 mg to about 600 mg.

16. A method of preserving musculoskeletal health in humans or animals comprising administering to the humans or animals in need thereof chondroitin sulfate of claim 1.

17. A pharmaceutical composition comprising the chondroitin sulfate of claim 1 and a pharmaceutically or nutraceutically acceptable excipient.

* * * * *